US006324481B1

(12) United States Patent
Atchison et al.

(10) Patent No.: US 6,324,481 B1
(45) Date of Patent: Nov. 27, 2001

(54) METHOD FOR THE CALCULATION OF WAFER PROBE YIELD LIMITS FROM IN-LINE DEFECT MONITOR DATA

(75) Inventors: Nick Atchison, Santa Cruz; Ron Ross, Scotts Valley, both of CA (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 09/333,713

(22) Filed: Jun. 15, 1999

Related U.S. Application Data

(60) Provisional application No. 60/105,139, filed on Oct. 21, 1998.

(51) Int. Cl.[7] ............................. G01N 37/00; G06F 19/00
(52) U.S. Cl. ............................. 702/84; 438/14; 700/121; 700/110
(58) Field of Search ................................... 702/35, 36, 40, 702/81–84, 170, 172, 118, 108, 117, 179, 181; 438/14; 700/110, 121

(56) References Cited

U.S. PATENT DOCUMENTS

| | | |
|---|---|---|
| 5,440,478 | 8/1995 | Fisher et al. . |
| 5,479,340 | 12/1995 | Fox et al. . |
| 5,483,468 | 1/1996 | Chen et al. . |
| 5,598,341 | 1/1997 | Ling et al. . |
| 5,777,901 | 7/1998 | Berezin et al. . |
| 5,793,650 * | 8/1998 | Mirza ..................... 702/34 |
| 5,862,054 | 1/1999 | Li . |
| 5,917,332 * | 6/1999 | Chen et al. ............. 324/765 |
| 5,946,213 * | 8/1999 | Steffan et al. .......... 700/110 |
| 5,991,699 * | 11/1999 | Kulkami et al. ........ 702/83 |
| 6,002,989 * | 12/1999 | Shiba et al. ............. 702/84 |
| 6,017,771 * | 1/2000 | Yang et al. ............. 438/7 |
| 6,035,244 * | 3/2000 | Chen et al. ............. 700/110 |
| 6,091,249 * | 7/2000 | Talbot et al. ........... 324/751 |
| 6,154,711 * | 11/2000 | Steffan et al. .......... 702/82 |
| 6,169,960 * | 1/2001 | Ehrichs ................... 702/36 |
| 6,185,511 * | 2/2001 | Steffan et al. .......... 702/81 |
| 6,223,098 * | 4/2001 | Cheong et al. ......... 700/223 |
| 6,256,593 * | 7/2001 | Damon et al. .......... 702/84 |

OTHER PUBLICATIONS

Kaiyuan Huang, Vinod K. Agarwal, K. Thulasiraman, "Diagnosis of Clustered Faults and Wafer testing", Feb. 1998, IEEE Transactions on Computer–Aided Design of Integrated Circuits and Systems, vol. 17, No. 2, pp. 136–148.*

R.E. Langford, J.J. Liou, "Nagative Binomial Yield Model Parameter Extraction Using Wafer Probe Bin Map Data", Jun. 1998, IEEE pp. 130–148.*

James Cunningham "The Use and Evaluation of Yield Models in Integrated Circuit Manaufacturing", May 1990. IEEE Transactions on Semiconductor Manufacturing, vol. 3, No. 2, pp. 60–71.*

Allan Wong, "Statistatical micro yielding modeling", Semiconductor International, vol. 19, Issue 12, Nov. 1996, pp. 139–148.*

Kevin Zinke "Yield Enhancement Techniques Using Neural Network Pattern Detection", Jul. 1997, IEEE/SEMI Advanced Semiconductor Manufacturing Conference, pp. 211–213.*

(List continued on next page.)

*Primary Examiner*—Marc S. Hoff
*Assistant Examiner*—Demetrius Pretlow
(74) *Attorney, Agent, or Firm*—W. Daniel Swayze, Jr.; W. James Brady; Frederick J. Telecky, Jr.

(57) ABSTRACT

A method of calculating yield limits for a factory to process semiconductor wafers, including the steps of generating a wafer map from the semiconductor wafers, eliminating die on said wafer map from consideration that have multiple defects, calculating killer probability for each of said die having only one defect, and predicting yield limits from said killer probabilities.

1 Claim, 5 Drawing Sheets

OTHER PUBLICATIONS

Ronald Harri, Anil Gandhi, Estimates of Integrated Circuit Yield Components form In–line Inspection Data and Post–process Sort Data, Jul. 1997, IEEE/SEMI Advanced Semiconductor Manufacturing Conference, pp. 150–155.*

"Integrated Circuit Yield Management and Yield Aanlaysis: Development and Implementation," by Charles H. Stapper and Raymond J. Rosner, IEEE Transactions on Semiconductor Manufacturing, vol. 8, No. 2, May 1995.

* cited by examiner

METHOD FOR THE CALCULATION OF WAFER PROBE YIELD LIMITS FROM IN-LINE DEFECT MONITOR DATA

CROSS-REFERENCES TO RELATED APPLICATIONS

This application claims benefit of Prov. No. 60/105,139 filed Oct. 21, 1998.

The copending patent application bearing Ser. No. 09/334,057, titled "An Improved Computer Program for Calculation of Parametric Yield Limits," filed Jun. 15, 1999, is incorporated by reference in its entirety.

The copending patent application bearing U.S. Pat No. 6,210,983, titled "Method for Analyzing Probe Yield Sensitivities to IC Design," filed Jun. 15, 1999, is incorporated by reference in its entirety.

The copending patent application bearing Ser. No. 09/333,717, titled "Method of a Comprehensive Sequential Analysis of the Yield Losses of Semiconductor Wafers," filed Jun. 15, 1999, is incorporated by reference in its entirety.

The copending patent application bearing Ser. No. 09/ 333,848, titled "A New Method for Wafer Zone Based Yield Analysis," filed Jun. 15, 1999, is incorporated by reference in its entirety.

FIELD OF THE INVENTION

The present invention generally relates to semiconductor wafer manufacture in the presence of particle contamination, and more particularly to the field of yield forecasting in a real-time semiconductor wafer manufacturing environment.

BACKGROUND OF THE INVENTION

Fabrication of semiconductor integrated circuits (ICs) is an extremely complex process that involves several hundred or more operations. They are fabricated by selectively implanting impurities into and applying conductive and insulative layers onto a semiconductor substrate. Semiconductor ICs (chips) are not manufactured individually but rather as an assembly of a hundred or more chips on a "wafer," which is then diced up to produce the individual chips.

Increasing production yield is an ongoing problem in the manufacture of semiconductor chips. Because of various defects that can occur in the fabrication of a wafer, a significant number of wafer die have to be discarded for one reason or another, thereby decreasing the percentage yield per wafer and driving up the cost of the individual chips. Defects are typically caused by foreign particles, minute scratches, and other imperfections introduced during photoresist, photomask, and diffusing operations. Yield impacts the number of wafer starts at the inception of production needed to meet specific customer order quantities for finished chips at the end of the production line. With the high demand for semiconductor chips and more orders than can possibly be filled by a production facility, predicting yield to accurately gauge wafer starts and utilizing defect information to remove yield-detracting operations are important aspects of improving the efficiency and hence the output of the fabrication facility.

Wafer-scanning tools are utilized to identify defects that occur in the chip manufacturing process for the aforementioned purposes. Typically, such tools are located at a variety of positions along the production line and include automated-vision inspection stations for identifying visual irregularities in the wafer die as they move through the line. The irregularities, i.e., defects, are recorded according to their coordinates, estimate of size, or other parameters and are stored as records in a database. The records represent raw information that is then analyzed or otherwise processed offline to determine the impact, if any, of the identified defects on product yield. Some defects, for example, may not adversely affect yield as much as others, and correspondingly must be classified differently for analysis purposes.

Commercially available wafer scanning tools include those made by KLA Instruments Corporation of Santa Clara, Calif.; Tencor Instruments Corporation of Mountain View, Calif.; Inspex, Inc. of Billerica, Mass.; and numerous other manufacturers. Despite significant advances made in wafer-scanning technology, the various tools that are available suffer striking deficiencies. In particular, such tools lack the capability to perform certain advanced classification and analysis of defect information necessary to accurately determine the true impact of wafer defects on yield. While conventional tools offer simple data presentation capabilities, such as the display of wafer maps, histograms and charts, they do not adequately classify or process the defect data.

More specifically, a disadvantage suffered by scanning tools is that they do not adequately perform yield prediction operations beneficial in a manufacturing defect analysis, thereby limiting the utility. It is often desirable to further refine the defect data before manual inspection and classification of individual defects on the review station. Since each wafer can include so many defects, it would not be practical to manually review and classify each of them. It would be desirable to utilize a method to randomly choose a statistically meaningful sample, i.e., subset, of such defects for consideration.

Historically, the review station operator randomly picks sets of defects that seem interesting and then reviews and classifies them. However, it is difficult for humans to systematically choose defects for this purpose that will be representative of all of the defects on the wafer. Some review stations are equipped with the ability to randomly move to different defects which the operator can then review and classify. A problem though with conventional randomizing methods performed on review stations is that they are not necessarily accurate in representing a true sampling of the wafer. For example, picking defects at random tends to result in the inordinate picking of defects that are part of a big cluster, because there are more of them, while defects of other types and in other locations on the wafer are overlooked. Therefore, it would be desirable to adopt an automated and consistent method for randomly identifying for review defects of interest. This method could focus on defect subpopulations defined in terms of defect size ranges or, alternatively, in terms of locations on the wafer, so that the sample of defects chosen best reflects the conditions actually occurring on the wafer.

FIGS. 1 and 2 illustrate a semiconductor wafer 2, which includes five particles 4, and the semiconductor wafer 2' contains eleven particles 4'.

FIG. 3 illustrates a schematic illustration of a semiconductor device in a semiconductor wafer. Circuit conductor lines 6 and 8 are designed in the semiconductor wafer to conduct electrical signals independently of one another. Due to imperfections in the semiconductor wafer manufacturing process, particle 10 has been introduced between conductors 6 and 8. Particle 10 does not interfere with either of conductors 6 and 8 and will generally not affect the functionality (or yield) of the defect in the semiconductor wafer manufacturing process, the particle does not cause failure in the semiconductor device by disturbing signals flowing in conductors 6 and 8.

FIG. 4 is also a schematic illustration of a portion of a semiconductor device similar to the illustration of FIG. 3. However, in FIG. 4, particle 10' is much larger than particle 10 of FIG. 3. In this example, particle 10' is in contact with both conductors 6 and 8 at regions 12 and 14, respectively. If particle 10' is able to conduct electricity, the independent operation of conductors 6 and 8 will be jeopardized, creating cross-talk between conductors 6 and 8. If different devices are connected to conductors 6 and 8, a single particle 10' may destroy the two devices embedded in the semiconductor wafer. Accordingly, particle 10' is what is commonly known as a "killer defect" since particle 10' may kill or prevent the normal operation of the semiconductor device which utilizes conductors 6 and 8. While the presence or absence of killer defects may be determined, it is important to utilize the defect characteristics in a semiconductor wafer.

FIGS. 5 and 6 are schematic illustrations of a portion of a semiconductor device for providing some additional background information regarding semiconductor defects. In FIG. 5, semiconductor device conductor lines 16 and 18 are separated by the distance 20. During the manufacturing process, particle 22 is introduced in the semiconductor wafer due to manufacturing defects or imperfections. Particle 22 has a diameter 24 and center point 26 as illustrated. In the situation illustrated in FIG. 5, particle 22 is in contact only with conductor 16 and is unable to be extended to contact both conductors 16 and 18. Therefore, particle 22 is considered to be a non-killer defect. Note that in this situation, the position of center 26 of particle 22, identified by dashed line 30, is spaced apart from the center position 28 of conductors 16 and 18 by distance 32. As particle 22 moves closer toward conductor 18, the center 26 of particle 22 will also move closer to center 28 or conductors 16 and 18 as illustrated in FIG. 6.

As shown in FIG. 6, the center 26 of particle 22 has moved closer to the center 28 of conductors 16 and 20. This is illustrated by the distance between center 28 and center line 30' being 32' which is smaller than the distance 32 in FIG. 5. Particle 22 is in contact with both conductors 16 and 20 and, correspondingly, is considered a killer defect. Thus, as the center 26 of particle 22 is moved closer to center 28 of conductors 16 and 20, the particle 22 will become more likely a killer defect. This, of course, presumes that particle 22 is large enough to be in simultaneous contact with both conductors 16 and 20.

SUMMARY OF THE INVENTION

The present invention includes a method of calculating yield limits for a factory to process semiconductor wafers, including the steps of generating a wafer map from the semiconductor wafers, eliminating die on said wafer map from consideration that have multiple defects, calculating killer probability for each of said die having only one defect, and predicting yield limits from said killer probabilities.

DETAILED DESCRIPTION OF THE PRESENT INVENTION

The present invention provides two methods for calculating wafer probe yield limits for wafers which are inspected for defects at points during the process in which semiconductor chips are prepared from a wafer. The present invention employs a pattern recognition inspection tool such as KLA. The first method in accordance with the present invention uses size histograms for various types of classified defects and then uses the probability of failure for the wafer under consideration to calculate the critical area. Then, the yield limits are calculated using negative binomial yield model or any other appropriate model. The second method utilizes the actual killer probabilities; for example, the probability of having a killer defect for various types of defects and, again, the yield limits are calculated from the negative binomial model. The second method tends to give more accurate results. The present invention is able to use yield limit calculations to predict probe yield of the wafer within 1% under most circumstances and during most time periods unless some "event" unrelated to random defects occurs. The present invention relates to defects and how to calculate the yield limit for a defect detected by a pattern recognition inspection tool.

Figure 1:
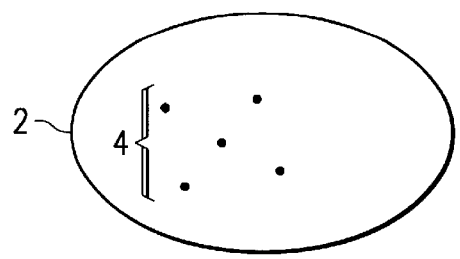
FIG. 1 is an illustration of a semiconductor wafer with a small particle count.
Figure 2:
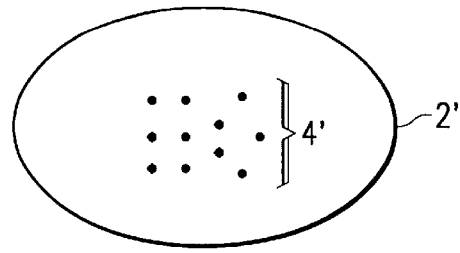
FIG. 2 is an illustration of a semiconductor wafer with a high particle count.
Figure 3:
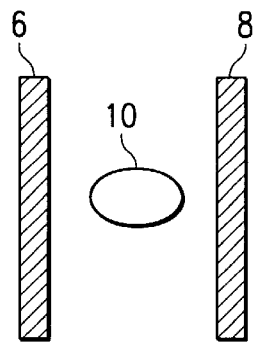
FIG. 3 is an illustration of a portion of a semiconductor device where no killer defects are experienced.
Figure 4:
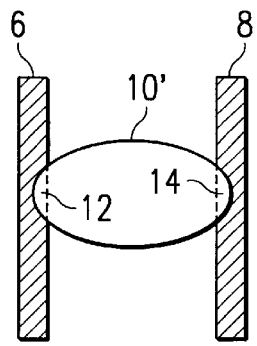
FIG. 4 is an illustration of a portion of a semiconductor device which has experienced a killer defect.
Figure 5:
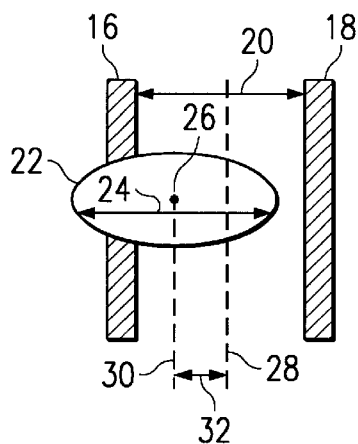
FIG. 5 is an illustration of a semiconductor device describing the relationship of the center of the particle and the center of the device conductors when no killer defect is present.
Figure 6:
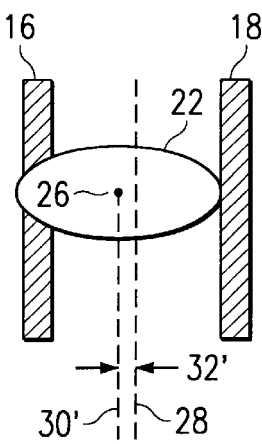
FIG. 6 is an illustration of a semiconductor device describing the relationship between the center of the particle and the center of the device conductors when a killer defect is present.
Figure 7:
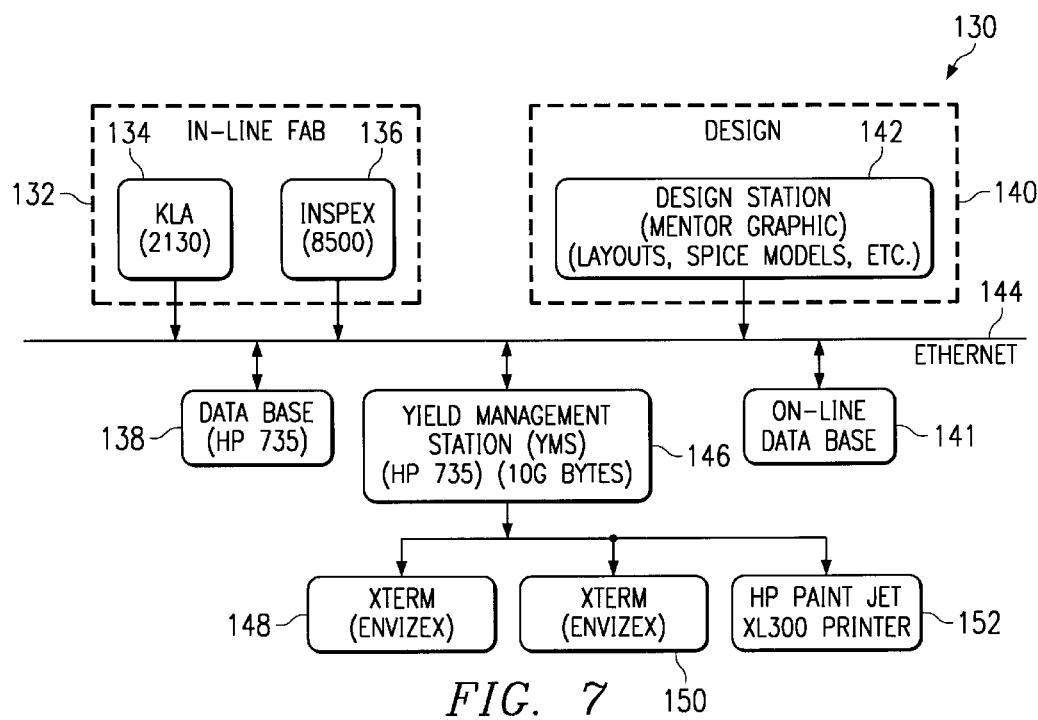
FIG. 7 is a block diagram illustrating a real-time in-line defect disposition and yield forecasting system.

FIG. 7 is a block diagram of the equipment in the real-time, in-line defect disposition and yield forecasting system. As shown in FIG. 7, the real-time, in-line defect disposition and yield forecasting system 130 includes an in-line fabrication equipment 132 which collects different particle sizes and locations of the particle sizes with respect to different layers in a semiconductor wafer. For example, the in-line fabrication equipment KLA 2130 manufactured by KLA Company in Sunnyvale, Calif., identified by reference numeral 134, or the INSPEX 8500 fabrication equipment manufactured by INSPEX Company in Boston, Mass., identified by reference numeral 136, may be used. The collected data is then transmitted via Ethernet drive transmission line 144 to data base 138. For example, the Hewlett Packard 735 computer includes such a function of collecting the data output from the in-line fabrication equipment 132 and storing for later retrieval.

In addition, the defect disposition and yield forecasting system 130 includes design station equipment 140 such as the design equipment 142 manufactured by Mentor Graphics in Oregon. Design station 142 is able to extract the various layouts for each layer in the semiconductor wafer as previously discussed. These layouts are then stored in data base 141 via Ethernet driven transmission line 144. The particle size and locations stored in data base 138 and the layout information stored in database 141 are then collected by the yield management station (YMS) 146 to determine the number and location of actual defects, as well as the defect sensitive area index for each of the layers in the semiconductor wafer under examination. Yield management station 146 can be, for example, Hewlett Packard's 735 computer with preferably 10 gigabytes of hard disk memory storage or more programmed in accordance with the present invention. The particle size and location information and layout information are then analyzed as described in connection with the present invention, the results of which are then displayed on monitors 148 and 150 or printed on printer 152. Examples of monitors 148 and 150 are the Exterm Display manufactured by Envizex. An example of the printer 152 is the Hewlett Packard Paint Jet XL300 printer.

Accordingly, the real-time in-line defect disposition and yield forecasting system is able to determine the number of actual defects caused for each layer of a semiconductor wafer and is also able to determine the defect sensitive area index for each layer of the semiconductor wafer. Using this detailed information, the real-time in-line defect disposition and yield forecasting system is able to accurately determine the status or condition of each layer of the semiconductor wafer to determine the layer which has the highest yield probability or possibility after inspection and analysis. Accordingly, the defect disposition and yield forecasting system is able to efficiently and effectively determine which layer of a semiconductor wafer requires inspection and analysis to correct device defects. The defect disposition and yield forecasting system is consequently able to optimize the amount of device defects in accordance with the present invention which may be corrected for different layers in the semiconductor wafer.

In order to calculate accurate yield limits for a product, several criteria must be established. First, a sufficient number of wafers and lots of wafers must be inspected to statistically represent the behavior of the manufacturing line of the factory. This number can be calculated using statistical methods and depends on the variability of the defect levels in the factory. Second, inspections must be staged through the process at critical steps where defects are most likely to cause yield loss. Third, a statistically significant number of defects per wafer should be reviewed or classified so that the defect type pareto accurately represents the population of wafers in the line. Finally, the area inspected on the wafers should closely match the total area tested at wafer probe.

Critical area is defined for a given layer, for example metal 1, for a given type of failure, for example shorts or opens, for a wafer. It is defined as the mathematical product of the die area for that product times the probability of failure of the given type of failure.

The probability of failure is obtained from actual experience or from a computer simulation which uses the layout database for the layer in question and generates random x and y coordinate numbers. Then, defects are superimposed (the defects being defined as squares or circles) of a specified or predetermined diameter on the layout at these random locations. This process is repeated a substantial number of times, for example 1,000, although another number of times could easily be used, using the same size of defect. The program checks the results to see how many of the defects cause two lines to short together or causes an open. The probability of failure for the shorts or opens would then be the number of defects which caused the shorts or opens divided by the total number of defects generated. For example, if 150 of the defects would cause shorts out of a total of 2,000 generated, the probability of failure would be 0.075 (150/2000).

Figure 8:
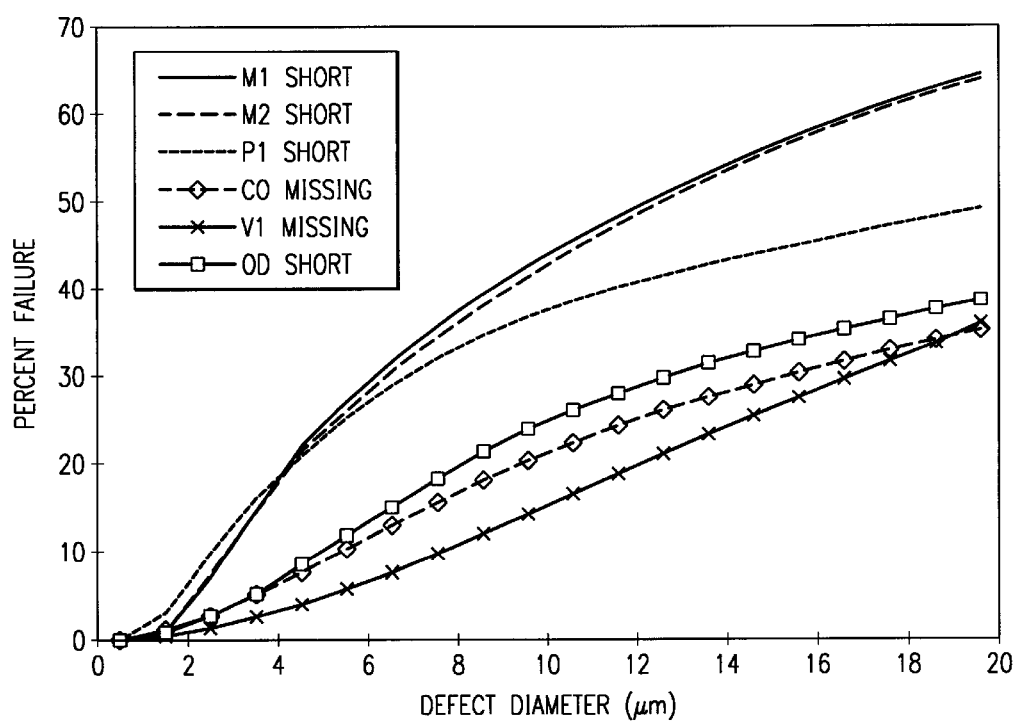
FIG. 8 illustrates the results of a simulation for probability of failure versus defect type.

The above procedure is repeated for different sizes of defects of interest, for example $1\mu$ to $20\mu$, in $1\mu$ increments. The probability of failure is then plotted versus the defect type. This process is repeated for each critical layer of the product. FIG. 8 shows the results of such a simulation for an actual wafer for several layers for shorts and for missing contacts and vias. Of course, similar graphs can be generated for opens, etc.

In order to calculate yield limits for a given product using the critical area concept, quantitative data is needed from the in-line defect inspection. The data that is generally required is actual defect densities (defects/unit area) by defect type and by layer. The defect density by defect type (for example, poly bridging, extra metal, etc.) must take into account the number of defects reviewed or classified versus the total number of defects on the wafer. A random sample of the defects should be reviewed. The formula for calculating the defect density is shown in Equation 1.

$$D_i = \frac{N_{R_i}}{N_R} * \frac{N_T}{A_T} \tag{1}$$

where:

$N_{R_i}$=The number of defects of type i in the sample under consideration $N_R$=The total number of defects reviewed on the wafers $N_T$=The total number of defects of all types detected in the inspection $A_T$=The total area inspected $D_i$=The defect density for defect classification i, which is known as the projected defect density.

Figure 9:
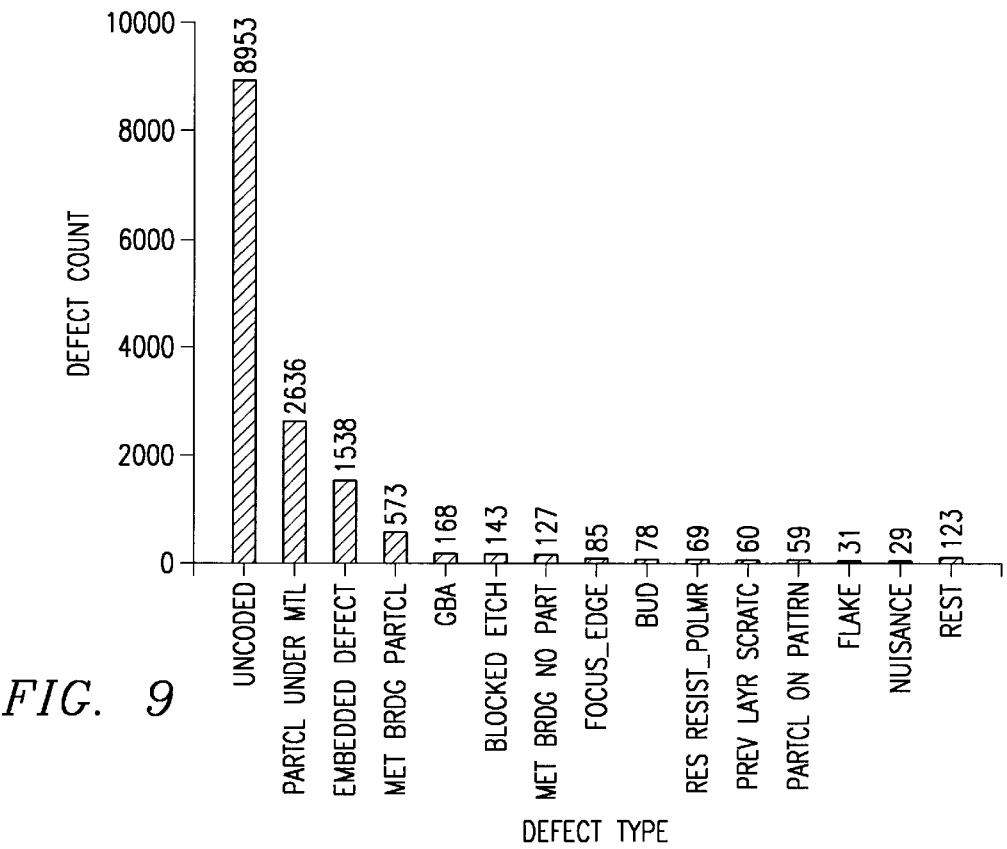
FIG. 9 illustrates a defect type pareto.

FIG. 9 illustrates an example of a defect type pareto in terms of projected defect density. The calculations found in the equation are made for unclustered defects only, because they are the ones to which the statistical distribution functions can be applied.

Figure 10:
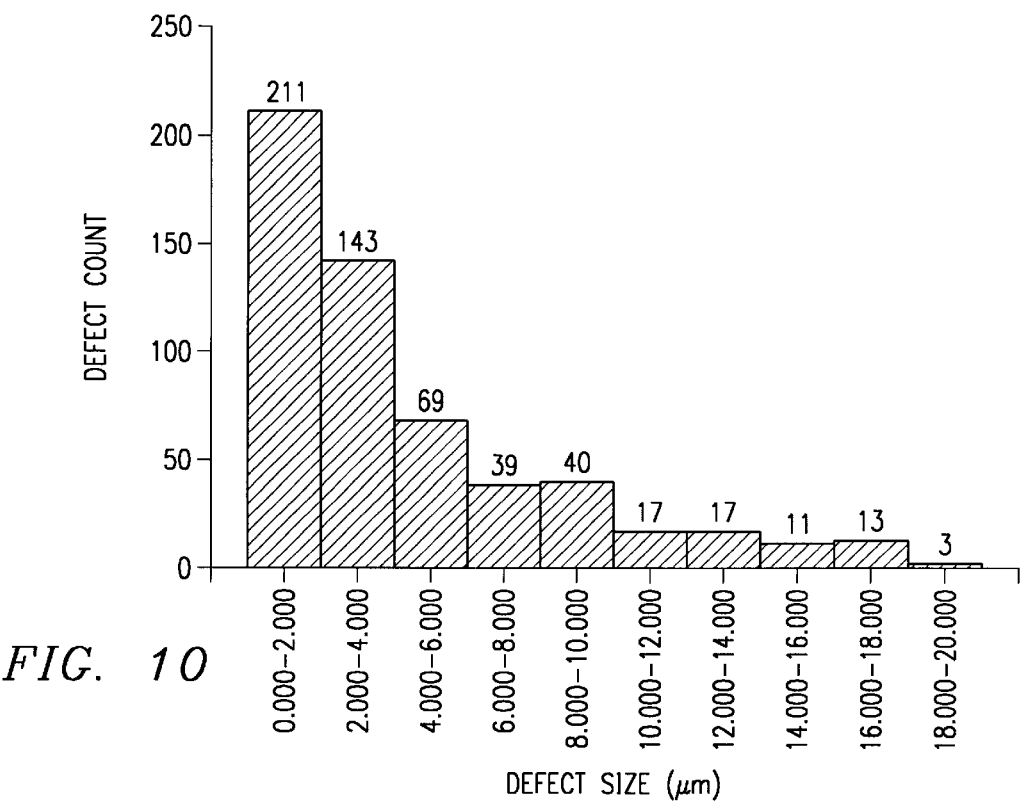
FIG. 10 illustrates a defect size distribution.

The defect size distribution for each type of defect is used to determine the yield limits. See FIG. 10. The present invention uses a negative binomial model:

$$Y_i = \frac{1}{\left(1 - \frac{\lambda_i}{\alpha}\right)^\alpha} \tag{2}$$

where $\alpha$ is the cluster factor and $\lambda$ is calculated from:

$$\lambda_i = \int_0^\infty (D_i(x) A_C(x)) dx \tag{3}$$

where:

x (the integration variable) is the defect size $D_i$ is the defect density $A_C$ is the critical area (obtained from the fail probability graphs)

The integral is evaluated numerically. The method assumes that the defects, once they land in a "critical" area where they can cause shorts or opens and if they are large enough, always cause failures (100% killer probability).

Therefore, only "adders" should be included in the calculations (adders are defects added since the prior inspection). This ensures that the same defects are not counted twice.

Another method of calculating yield limits due to random defects is to use actual defect-map-to-wafer-probe map overlays to determine killer probabilities. Wafer maps are generated by defect type (classification), and the maps for a specific wafer could be partitioned into the blocks representing the individual die.

One way to calculate the killer probability is to eliminate die that have multiple defects and calculate killer probabilities for each defect type for those die having only one defect from the simple ratio:

$$P_{k_i} = \frac{N_{D_i}}{N_{T_i}} \quad (4)$$

where $N_{D_i}$ is the number of die having defect type "i" that did not yield at wafer probe, and where $N_{T_i}$ is the total number of die on the inspected wafers that contained type "i" defects.

Using only the die that have a single defect performs well where all the yields are high and defect density is low. For example, if the total defect density at all inspection points is $1/cm^2$ and the die size is 1 $cm^2$, the probability of die having $\geq 1$ defect/die is 63.2% (for randomly distributed defects using the formula $e^{-AD}$) and the probability of die having $\geq 2$ defect/die would be 40%. This leaves 60% of the die with defects from which to calculate the killer probabilities. If the defect density were $2/cm^2$, then the probability of having $\geq 2$ defects on the die is 75% and only 25% of the die could be used in the calculations. For 4 defects/$cm^2$ the probability of $\geq 2$ defects would be 96% leaving only 4% of the die for killer probability calculations. If the defect density is normalized to average defects per unit die area (defect density/die area), it can be seen that as the ratio gets larger, the probability of having multiple defects/die becomes greater rapidly. For high defect densities, therefore, it is necessary to increase the sample size to achieve the same statistical confidence in the killer probability numbers or to use a more complex algorithm to calculate the killer probability. For the numbers given above, it would be necessary to use 15× the sample size for the defect density of 4/$cm^2$ as compared with the case of 1/$cm^2$. Once the killer probabilities have been calculated for each type of defect, the yield limits can be calculated from:

$$Y_i = \frac{1}{\left(1 + \frac{P_{k_i} D_{k_i} A}{\alpha}\right)^{\alpha}} \quad (5)$$

where:

$P_{k_i}$=killer probability for defect type "i"

$D_{K_i}$=defect density for defect type "i"

A=die area

Equation 5 is valid for unclustered defects.

Clustered defects can result from scratches, runs of photoresist, SOG droplets resulting from spinning the wafers, etc. The gross yield limits for clusters of defects can be calculated by overlaying clustered defects wafer maps with probe wafer maps. The formula for the yield limit is:

$$Y_i = 1 - \left(\frac{N_C * N_{AV}}{N * N_G}\right) * P_k \quad (6)$$

where:

$$P_{k_i} = \frac{N_{CD}}{N_D}$$

$P_{k_i}=$ $N_C$=Number of clustered defects $N_{AV}$=Average number of die affected per cluster $N_G$=Gross die per wafer $N_D$=Total number of die affected by clusters $N_{CD}$=Total number of die affected by clusters that were non-yielding N=Number of wafers inspected If the clusters are classified during the inspection, for example scratches or SOG bubble runs, then separate yield limits could be calculated for the various types of clusters.

Once the killer probability has been calculated and the average number of die affected per cluster has been determined, the above equation can be used to predict yield limits for lots inspected in the line which have not been tested. Obviously, the formula reduces to:

$$Y_C = 1 - \frac{\text{\# Dead\_Die\_at\_Probe\_due\_to\_Clusters}}{\text{Total\_Die\_Tested}}$$

$Y_c$=Cluster defect yield limit. The numerator indicates the number of die that contained clustered defects that failed wafer probe, which is determined from bin overlay maps.

The present invention finds it advantageous to track in-line defect monitor data in terms of actual yield loss to key products as opposed to raw defect density. If a particular class of defects has a low killer probability but the defect density is relatively high, it may be less beneficial to track.

Figure 11:
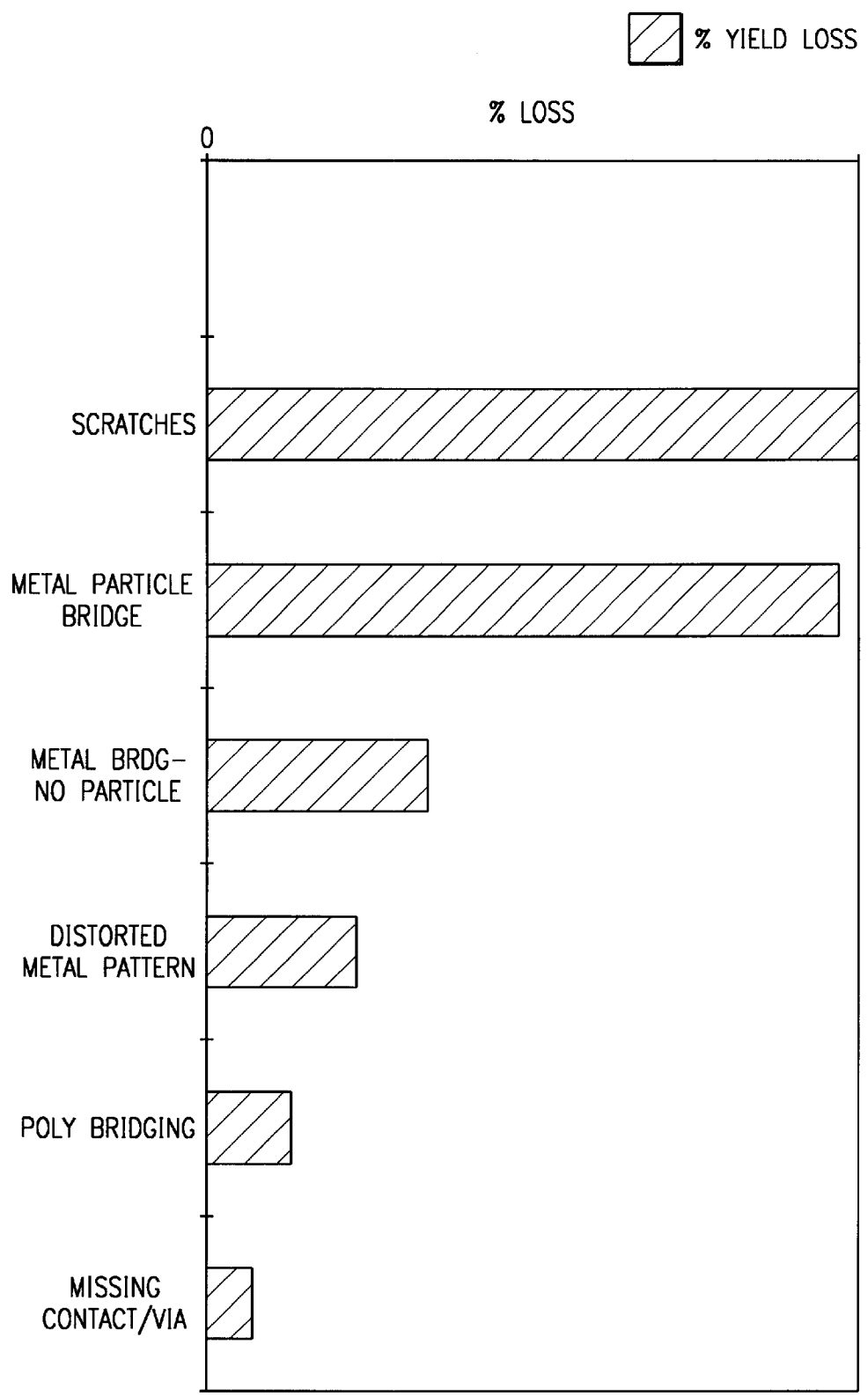
FIG. 11 illustrates a defect yield loss pareto.
Figure 12:
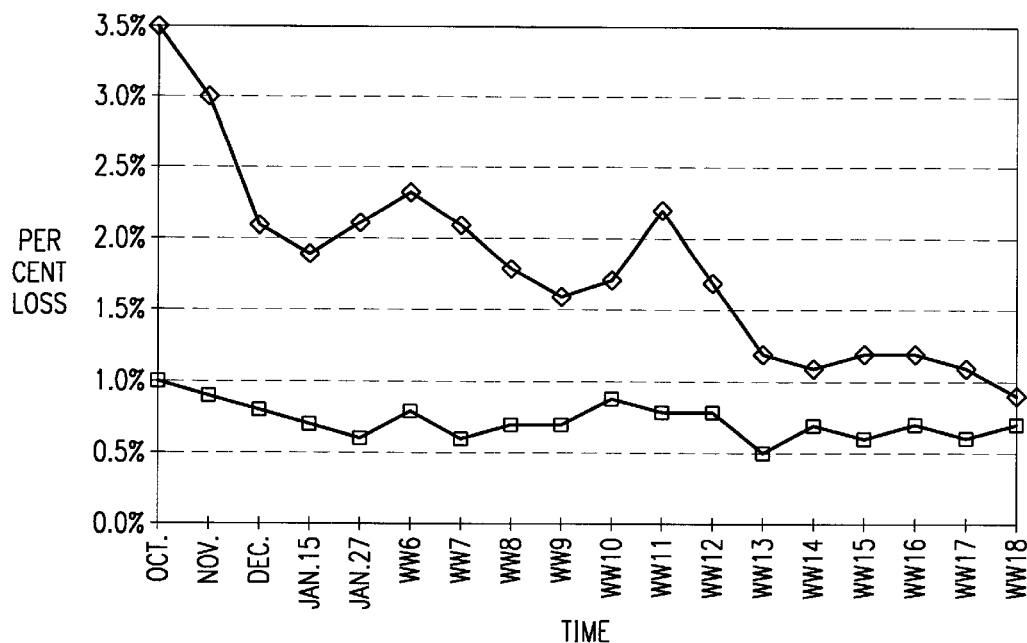
FIG. 12 illustrates a scratch yield loss trend.
Figure 13:
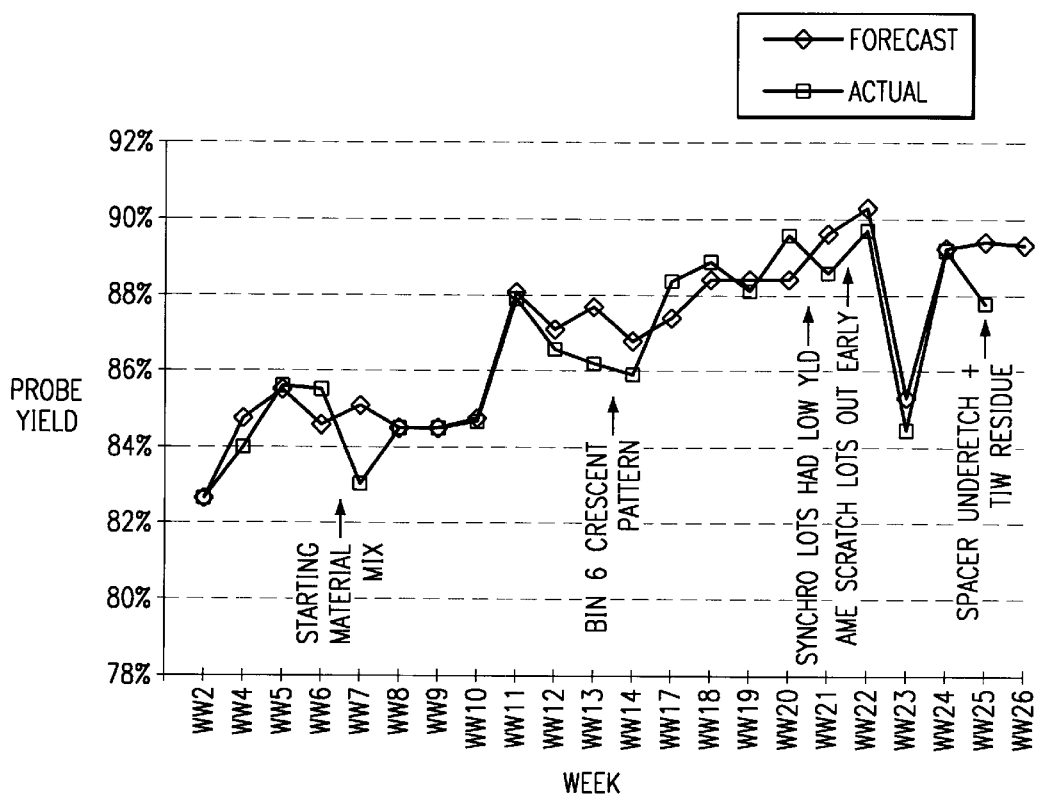
FIG. 13 illustrates an actual yield versus forecast.

FIG. 11 shows an example of a defect yield loss pareto by defect type for an actual wafer. This indicates that scratches and metal particle bridging would be the highest priority problems to work on. FIG. 13 shows a trend plot for scratches showing improvement over time as a team worked on the above mentioned problem.

The present invention has been used to track the yield limits of the manufacturing line and actually has been used to predict the yields for products expected for the next 1–2 weeks. This is based upon the assumption that systematic losses will remain the same. This is accomplished by inspecting a "representative" (statistically significant) sample of wafers for the wafer in question, using the "killer probability" method for calculating yield limits and calculating the overall yield by multiplying the individual limits together.

FIG. 13 illustrates a plot of the actual yield versus the predicted yield for a specific product over a specific time period. It can be seen that the predicted yield agrees well with actual yield with exceptions occurring when some event takes place, for example a systematic problem, which cannot be detected by the inspection tool.

The present invention produces calculations of product probe yield limits from in-line random defect inspection data by either the critical area method, using defect size histograms, and the killer probability method, using killer probabilities from defect map/wafer probe map overlays.

Killer probabilities provide a very accurate representation for the calculation. Such tracking makes it possible to properly prioritize yield improvement projects. Forecast yields are possible. The present invention provides a tool to improve the pinpointing of sources of yield loss. The method of this invention is an integral part of a general yield enhancement method that has had an influence of creating one of the highest yield manufacturing processes. Factory yields may increase by as much as 20% with the proper use of the overall yield improvement method.

What is claimed is:

1. A method of calculating yield limits for a factory to process semiconductor wafers, comprising the steps of:
   generating a wafer map from the semiconductor wafers;
   eliminating die on said wafer map from consideration that have multiple defects;
   calculating killer probability for each of said die having only one defect; and
   predicting yield limits from said killer probabilities.

* * * * *